(12) United States Patent
Fowler

(10) Patent No.: US 7,131,977 B2
(45) Date of Patent: Nov. 7, 2006

(54) APPARATUS AND METHOD FOR REMOVING A CLIP

(75) Inventor: David N. Fowler, Raleigh, NC (US)

(73) Assignee: Pilling Weck Incorporated, Limerick, PA (US)

( * ) Notice: Subject to any disclaimer, the term of this patent is extended or adjusted under 35 U.S.C. 154(b) by 538 days.

(21) Appl. No.: 10/228,746

(22) Filed: Aug. 27, 2002

(65) Prior Publication Data

US 2004/0044363 A1    Mar. 4, 2004

(51) Int. Cl.
    A61B 17/10    (2006.01)
    A61B 17/29    (2006.01)
(52) U.S. Cl. .................................. 606/138; 606/206
(58) Field of Classification Search .............. 606/1, 606/138, 139, 142, 143, 157, 158, 205–211
    See application file for complete search history.

(56) References Cited

U.S. PATENT DOCUMENTS

| | | | |
|---|---|---|---|
| 3,270,745 A | 9/1966 | Wood | |
| 3,326,216 A | 6/1967 | Wood | |
| 3,439,522 A | 4/1969 | Wood | |
| 3,439,523 A | 4/1969 | Wood | |
| 4,146,130 A | 3/1979 | Samuels et al. | |
| 4,509,518 A | 4/1985 | McGarry et al. | |
| 4,579,118 A * | 4/1986 | Failla | 606/158 |
| 4,834,096 A | 5/1989 | Oh et al. | 128/325 |
| 5,062,846 A | 11/1991 | Oh et al. | 606/158 |
| 5,100,416 A | 3/1992 | Oh et al. | 606/139 |
| 5,403,327 A | 4/1995 | Thornton et al. | 606/143 |
| 5,509,920 A | 4/1996 | Phillips et al. | 606/157 |
| 5,527,320 A | 6/1996 | Carruthers et al. | 606/143 |
| 5,634,930 A | 6/1997 | Thornton et al. | 606/143 |
| 5,722,982 A * | 3/1998 | Ferreira et al. | 606/151 |
| 6,391,035 B1 | 5/2002 | Appleby et al. | 606/142 |
| 6,406,485 B1 | 6/2002 | Hossain et al. | 606/207 |
| 2004/0044352 A1 * | 3/2004 | Fowler et al. | 606/142 |

FOREIGN PATENT DOCUMENTS

WO    97/39689    * 10/1997    ................. 606/143

* cited by examiner

Primary Examiner—Glenn K. Dawson
(74) Attorney, Agent, or Firm—Baker & Hostetler LLP

(57) ABSTRACT

An endoscopic apparatus includes a pair of jaws pivotably connected to each other and movable between an open position and a closed position. The jaws have respective opposing gripper portions. Each gripper portion has a distal end, a proximal end, and an inside surface extending between the distal and proximal ends. At the closed position, the inside surfaces define a jaw gap therebetween. At least a portion of the jaw gap increases in distance along a direction from the distal end toward the proximal end. An actuating mechanism communicates with the jaws for moving the jaws between the open and closed position. In a surgical procedure in which a clip such as a hemostatic clip has been latched around a blood vessel or other tissue, the apparatus can be used to compress the clip and consequently unlatch the clip, thereby releasing the clip from the vessel. Thereafter, the apparatus can be rotated. After rotation, the apparatus can be used to grasp the clip and subsequently remove the clip from the surgical site.

17 Claims, 15 Drawing Sheets

APPARATUS AND METHOD FOR REMOVING A CLIP

TECHNICAL FIELD

The present invention generally relates to the design and use of instruments adapted for manipulating small objects such as surgical clips. More specifically, the present invention relates to surgical endoscopic instruments that can be actuated to unlatch clips from a surgical site such as a ligature and subsequently extract such clips from the surgical site.

BACKGROUND ART

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. In many procedures, the clip is left in place permanently after application to the tissue. In other cases, the clip must be removed because, for example, only temporary occlusion of a vessel is desired, or the clip has been mistakenly latched to a structure that is not to be ligated. In these latter cases, the clip is removed by using a separate instrument dedicated for that purpose, i.e., a clip removal instrument.

Ligating clips can be classified according to their geometric configuration (e.g., symmetric clips or asymmetric clips), and according to the material from which they are manufactured (e.g., metal clips or polymeric clips). Symmetric clips are generally "U", "V" or "C" shaped and thus are substantially symmetrical about a central, longitudinal axis extending between the legs of the clip. Symmetric clips are usually constructed from metals such as stainless steel, titanium, tantalum, or alloys thereof. By means of a dedicated clip applier, the metal clip is permanently deformed over the vessel. An example of one such clip is disclosed in U.S. Pat. No. 5,509,920 to Phillips et al. An example of a metallic clip applier is disclosed in U.S. Pat. No. 3,326,216 to Wood, in which a forceps-type applier having conformal jaws is used to grip and maintain alignment of the clip during deformation. Such appliers may additionally dispense a plurality of clips for sequential application, as disclosed for example in U.S. Pat. No. 4,509,518 to McGarry et al.

With the advent of high technology diagnostic techniques using computer tomography (CATSCAN) and magnetic resonance (MRI), metallic clips have been found to interfere with the imaging techniques. To overcome such interference limitations, biocompatible polymers have been increasingly used for surgical clips. Unlike metallic clips, which are usually symmetric, polymeric clips are usually asymmetric in design and hence lack an axis of symmetry. Inasmuch as a plastic clip cannot be permanently deformed for secure closure around a vessel or other tissue, latching mechanisms have been incorporated into the clip design to establish closure conditions and to secure against re-opening of the vessel. For example, polymeric clips are disclosed in U.S. Pat. No. 4,834,096 to Oh et al. and U.S. Pat. No. 5,062,846 to Oh et al., both of which are assigned to the assignee of the present invention. These plastic clips generally comprise a pair of curved legs joined at their proximal ends with an integral hinge or heel. The distal ends of the curved legs include interlocking latching members. For example, the distal end of one leg terminates in a lip or hook structure into which the distal end of the other leg securely fits to lock the clip in place. The distal ends of the clips taught by Oh et al. also include lateral bosses that are engaged by conformal recesses of the jaws of the clip applier. A clip applier specifically designed for asymmetric plastic clips is used to close the clip around the tissue to be ligated, and to latch or lock the clip in the closed condition. In operation, the jaws of this clip applier are actuated into compressing contact with the legs of the clip. This causes the legs to pivot inwardly about the hinge, thereby deflecting the hook of the one leg to allow reception therein of the distal end of the other leg. A clip applier designed for use with asymmetric plastic clips in an open (i.e., non-endoscopic) surgical procedure is disclosed in U.S. Pat. No. 5,100,416 to Oh et al., assigned to the assignee of the present invention.

In addition to compatibility with sophisticated diagnostic techniques, asymmetric clips have other advantages over symmetric clips. For example, because asymmetric clips are formed from polymeric materials, the mouths of asymmetric clips can be opened wider than the mouths of symmetric clips. This allows a surgeon to position the clip about the desired vessel with greater accuracy. In addition, a clip of the type described in above-cited U.S. Pat. Nos. 4,834,096 and 5,062,846 can be repositioned before locking the clip on the vessel or before removing the clip from the vessel, in a process referred to as "approximating" the clip.

As indicated above, instruments employed to install metal and polymeric clips are solely dedicated to the clip applying function, and thus cannot be reversely operated to remove the clip once applied. Accordingly, separate tools have been employed for the sole purpose of reversely deforming and removing clips. In the past, a satisfactory instrument for removing latching polymeric clips had not been available. In past instances where a surgeon desired to remove or relocate the clip, the clip had to be physically severed by appropriate cutting instruments, such as scalpels, scissors and the like. Such removal techniques require substantial time and dexterity to safely remove the clip without adverse consequences to surrounding tissue. Accordingly, a need arose for developing a surgical instrument for removing plastic latching clips in a manner that released the clip from a latched condition in a single piece without destruction of the clip and damage to surrounding tissue. In the case of open surgery, these problems have been addressed by an open, forceps-type clip removal instrument disclosed in U.S. Pat. No. 6,391,035 to Appleby et al., assigned to the assignee of the present invention. The need remains, however, for a polymeric clip removing instrument having an improved jaw design to enable better handling of and control over such clips, as well as for a clip removing instrument suitable for use in endoscopic-type surgical procedures, particularly an instrument that successfully addresses the problems attending the use of asymmetric clips.

As a general matter, laparoscopic, endoscopic, and other minimally invasive surgical techniques enable surgeons to perform complex procedures through relatively small entry points, or surgical ports, in the body. The term "laparoscopic" refers to surgical procedures performed on the interior of the abdomen, while the term "endoscopic" refers more generally to procedures performed in any portion of the body. Endoscopic surgery involves the use of an endoscope, which is an instrument permitting the visual inspection and magnification of a body cavity. The endoscope is inserted into a body cavity through a cannula extending through a hole or port in the soft tissue protecting the body cavity. The port is typically made with a trocar, which includes a cutting instrument slidably and removably disposed within a trocar cannula. After forming the port, the cutting instrument can be withdrawn from the trocar cannula. A surgeon can then perform diagnostic and/or therapeutic procedures at the surgical site with the aid of specialized medical instruments adapted to fit through the trocar cannula and additional trocar cannulas providing openings into the desired body cavity.

Some known advantages of minimally invasive surgical techniques include reduced trauma to the patient, reduced likelihood of infection at the surgical site, and lower overall medical costs. Accordingly, minimally invasive surgical techniques are being applied to an increasingly wider array of medical procedures.

Surgical clip appliers and removers adapted for endoscopic surgical techniques typically include a shaft that is inserted through an endoscopic cannula to access a surgical site in a body cavity and a jaw assembly disposed at the distal end of the shaft for manipulating a surgical clip at the surgical site. The basic operations of endoscopic clip appliers and removers are as indicated above. The clip applier is used to position the clip over the desired vessel and its jaws are actuated, typically using an actuating mechanism disposed in the handle of the device, to close the clip about the vessel. In certain cases such as those previously mentioned, the clip remover can be used to unlatch the clip.

As endoscopic techniques have been developed, certain inadequacies in the available surgical equipment have become apparent. For example, the jaws of the removing instrument, which are typically used to disengage the clip from the vessel, may exert unequal pressure on the clip, resulting in a "scissoring" effect and damage to the vessel. In addition, the jaws may impart excessive force on the clip and consequently crush the clip, thereby creating a risk that pieces of the clip are not removed from the body cavity. In prior art devices, the force applied to the clip has been difficult to control by the surgeon using the clip removal instrument. In other instances, the clip may not be properly oriented when it is placed within the jaws, or may slip out of alignment or even be ejected from the jaws during use of the removal instrument. This can result in the loss and/or crushing of the clip or pieces thereof, damage to tissue, or otherwise unsuccessful use of the removal instrument.

Moreover, existing clip removal instruments have been designed primarily for manipulating symmetric clips, and therefore are not well suited to satisfy design issues unique to asymmetric clips. For example, when symmetric clips are closed on a vessel, the opposing legs of the clip apply substantially even pressure to the opposing sides of the vessel. By contrast, the opposing legs of an asymmetric clip can apply varying pressure to opposing sides of a vessel when the asymmetric clip is closed. Thus, ideally a clip removal instrument should be designed to account for the asymmetry of the clip, so as to avoid the above-mentioned unequal pressure on the clip and resulting damage to the vessel. Further, lockable asymmetric clips generally function best when force is applied at or near the distal ends of the clip legs. Still further, asymmetric clips usually need to be placed under compression to be unlatched. Conventional clip removal instruments designed for symmetric clips may not provide the ability to adequately compress or approximate a clip.

As an additional problem, while clip removers of the prior art are capable of unlatching the clip, once the clip has been unlatched, the same instruments are not additionally capable of actually removing the clip from the surgical site and subsequently extracting the clip from the body cavity through the surgical port. An additional clip-grasping instrument has conventionally been required for this purpose. It therefore would be advantageous to provide a clip removal instrument that is capable of both unlatching the clip as well as grasping the clip for extraction from the surgical site.

In view of the foregoing discussion, a need is acknowledged by persons skilled in the art to provide an endoscopic clip removing apparatus that enables improved control over manipulation of a clip, especially a surgical clip and particularly one of asymmetric design. A further need is acknowledged to provide an endoscopic clip removing apparatus that, in use, prevents the clip from being crushed, especially polymeric clips that are more prone to breaking in comparison to metal clips, and prevents damage to tissue. A still further need is acknowledged to provide an endoscopic clip removing apparatus that is capable of not only unlatching a clip but also thereafter removing the clip from the surgical site.

DISCLOSURE OF THE INVENTION

According to one embodiment of the present invention, an endoscopic apparatus for unlatching a clip comprises first and second jaws pivotably connected to each other and movable between an open position and a closed position, and an actuating mechanism communicating with the first and second jaws for moving the jaws between the open and closed positions. The first and second jaws comprise respective opposing first and second gripper portions. Each gripper portion comprises a distal end, a proximal end, and an inside surface extending between the distal and proximal ends. At the closed position, the inside surfaces define a jaw gap therebetween. At least a portion of the jaw gap increases in distance along a direction from the distal ends towards the proximal ends.

According to one aspect of this embodiment, the inside surface of each gripper portion comprises a first frictional section disposed near the distal end of the respective gripper portion, a second frictional section disposed near the proximal end of the respective gripper portion, and a smooth section between the first and second frictional sections. Preferably, each frictional section comprises a plurality of serrations, grooves, teeth, or the like. The smooth sections can be provided by means of a polishing process.

According to another aspect of this embodiment, an elongate member interconnects the jaws and the actuating mechanism and is actuatable by the actuating mechanism.

According to yet another aspect of this embodiment, a sleeve is coaxially disposed about the elongate member. Advantageously, the sleeve is connected to the jaws so as to be rotatable along the elongate member, such that rotation of the sleeve causes rotation of the jaws. It is also advantageous that the sleeve comprise a fluid outlet disposed near the jaws, a fluid inlet axially spaced from the fluid outlet, and an annular fluid passage defined between the sleeve and the elongate member that communicates with the fluid inlet and the fluid outlet to provide a flushing mechanism for the apparatus.

Preferably, the actuating mechanism comprises an actuator pin extending through the first and second jaws. The actuator pin is movable between a distal position that corresponds to the open position of the first and second jaws, and a proximal position that corresponds to the closed position of the first and second jaws.

According to another embodiment of the present invention, an endoscopic apparatus for unlatching a clip comprises a pair of pivotably connected jaws, an axially movable actuator pin extending through the jaws, and a reciprocable rod connected to the actuator pin. The jaws comprise respective opposing distal ends, proximal ends and inside surfaces. Each inside surface includes a proximal rough section and a smooth section distally adjacent to the proximal rough section. At the closed position, a jaw gap defined between the inside surfaces increases in distance in a direction from the distal ends toward the proximal ends. Axial movement of the actuator pin causes rotational movement of the jaws between the open and closed positions.

According to any of the above embodiments of the present invention, an advantage is provided wherein, at the closed position of the jaws, the respective inside surfaces of the jaws do not contact each other. According to this aspect, the jaw gap exists between the jaws even at the respective distal ends thereof when the jaws are at the closed position.

The present invention also provides a method for unlatching a clip that is initially provided in a latched state. Such a clip typically comprises first and second legs joined at a hinge region of the clip. The first and second legs have respective distal end members that, in the latched state, are engaged with each other to define an interlocked clip region. According to the method, first and second jaws are provided. The jaws are pivotably connected to each other and are movable between an open position and a closed position. The first jaw comprises a first distal jaw end, a first proximal jaw end, and a first inside surface extending between the first distal jaw end and the first proximal jaw end. The second jaw comprises a second distal jaw end, a second proximal jaw end, and a second inside surface extending between the second distal jaw end and the second proximal jaw end. At the closed position, the inside surfaces define a jaw gap therebetween. At least a portion of the jaw gap increases in distance along a direction from the respective distal jaw ends toward the proximal jaw ends. The clip is engaged with the first and second jaws. The engagement is accomplished by bringing the first jaw into contact with the first leg of the clip and the second jaw into contact with the interlocked clip region and hinge region, with the hinge region being disposed near the second proximal jaw end. The clip is compressed by moving the first and second jaws toward their closed position, whereby the respective distal end members of the first and second legs of the clip become separated.

This method is particularly advantageous for manipulating clips of the type wherein the first and second legs of the clip are arcuate, and a concave inside surface of the first leg faces a convex inside surface of the second leg. The method is also particularly advantageous for manipulating clips that are constructed from a polymeric material. The method is further advantageous for manipulating clips of the type wherein the distal end member of the first leg of the clip comprises a hook region, and the distal end member of the second leg is retained by the hook region to define the interlocked clip region in the latched state of the clip. During the clip engaging step, the second jaw contacts the hook region of this clip.

According to another aspect of this method, the step of engaging the clip comprises bringing a frictional section of the second inside surface of the second jaw into contact with the hinge region to prevent the clip from becoming disengaged from, or misaligned in, the first and second jaws during the compressing step.

According to another aspect of this method, the step of engaging the clip comprises bringing a first smooth section of the first inside surface of the first jaw into contact with the first leg of the clip to prevent the clip from being damaged during the compressing step, whereby the first leg is slidable along the first smooth section during the compressing step.

According to still another aspect of this method, the step of engaging the clip comprises bringing a second smooth section of the second inside surface of the first jaw into contact with the interlocked clip region to prevent the clip from being damaged during the compressing step, whereby the interlocked clip region is slidable along the second smooth section during the compressing step.

According to an additional aspect of this method, the jaws are also employed to remove the clip after the clip has been unlatched. Removal of the clip is accomplished according to the following step. The first and second jaws are disengaged from the clip. The first and second jaws are rotated. The clip is grasped with the first and second jaws by bringing the first jaw into contact with a first side of the hinge region of the clip and a second jaw into contact with opposing side of the hinge region. The first and second jaws can be rotated by rotating an elongate member attached to the first and second jaws.

According to an additional aspect of this method, the step of grasping the clip comprises bringing a first frictional section of the first inside surface of the first jaw into contact with the first side of the hinge region, and bringing a second frictional section of the second inside surface of the second jaw into contact with the second opposing side of the hinge region.

According to another aspect of this method, an area at which the clip is initially disposed is flushed by conveying a fluid through a sleeve that is attached to the first and second jaws. The fluid is conveyed to an outlet aperture of the sleeve that is disposed near the first and second jaws.

In another method of the present invention for unlatching a clip that is initially provided in a latched state, the clip is of the type that comprises first and second arcuate legs joined at a hinge section. The first leg terminates at a hook section and the second leg terminates at an end section retained by the hook section in the latched state. The method provides first and second jaws that are pivotably connected to each other and movable between an open position and a closed position. At the closed position, the first and second jaws define a jaw gap therebetween. At least a portion of the jaw gap increases in distance along a direction from a distal end of the jaws toward a proximal end of the jaws. The clip is engaged with the first and second jaws. This is accomplished by bringing the first jaw into contact with the first leg of the clip and the second jaw into contact with the hook and hinge sections of the clip, with the hinge section contacting a proximal frictional section of the second jaw. The clip is compressed by moving the first and second jaws toward their closed position, whereby the first leg of the clip begins to straighten and the end section of the second leg is released from the hook section of the first leg.

It is therefore an object of the present invention to provide an endoscopic clip removing apparatus that enables improved control over manipulation of a clip.

It is another object of the present invention to provide an endoscopic clip removing apparatus that is compatible for manipulating surgical clips, especially those of asymmetric design and which are constructed from a polymeric material.

It is yet another object of the present invention to provide an endoscopic clip removing apparatus that prevents the clip from being crushed and prevents damage to tissue during operation of the apparatus.

It is still another object of the present invention to provide an endoscopic clip removing apparatus that is capable of both unlatching a clip and thereafter removing the clip from the surgical site.

Some of the objects of the invention having been stated hereinabove, and which are achieved in whole or in part by the present invention, other objects will become evident as the description proceeds when taken in connection with the accompanying drawings as best described hereinbelow.

DETAILED DESCRIPTION OF THE INVENTION

In the following description of the present invention, the term "remove" is used to mean the process of unlatching a clip, grasping an unlatched clip, retrieving or extracting an unlatched clip from a surgical site such as through an endoscopic-type pathway, and/or a combination of these procedural steps.

Figure 1A:
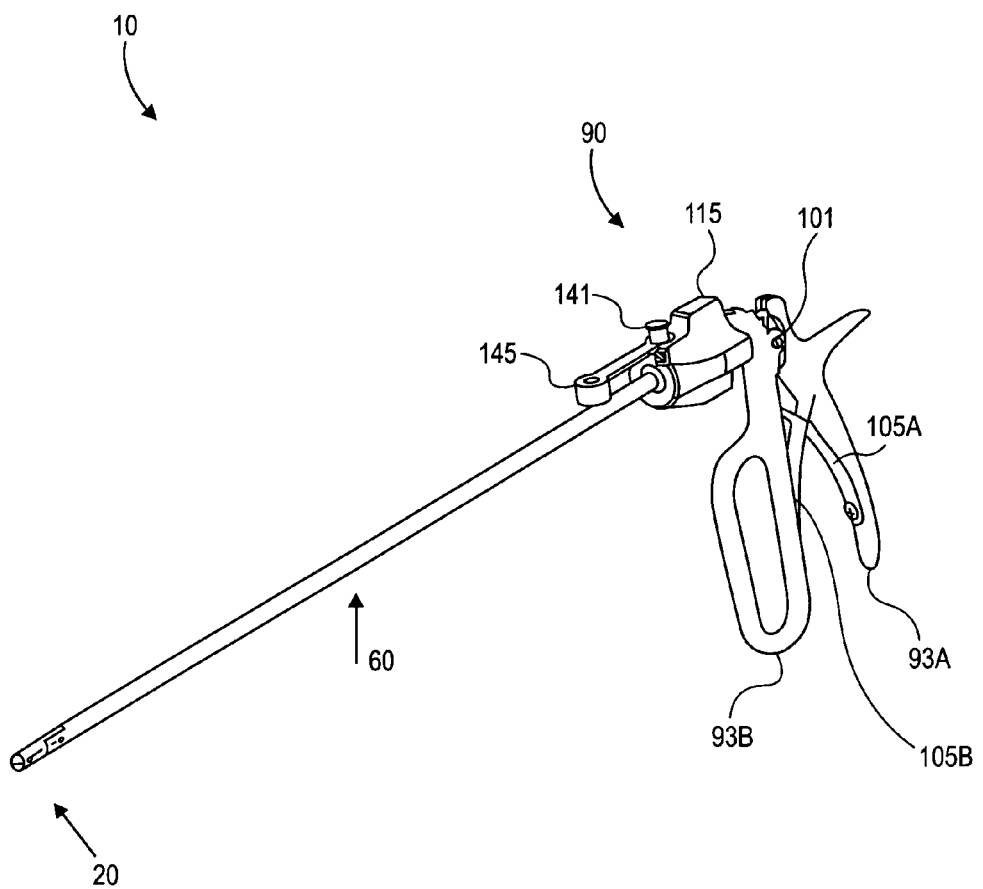
FIG. 1A is a perspective view of an endoscopic surgical clip removing apparatus provided in accordance with the present invention.
Figure 1B:
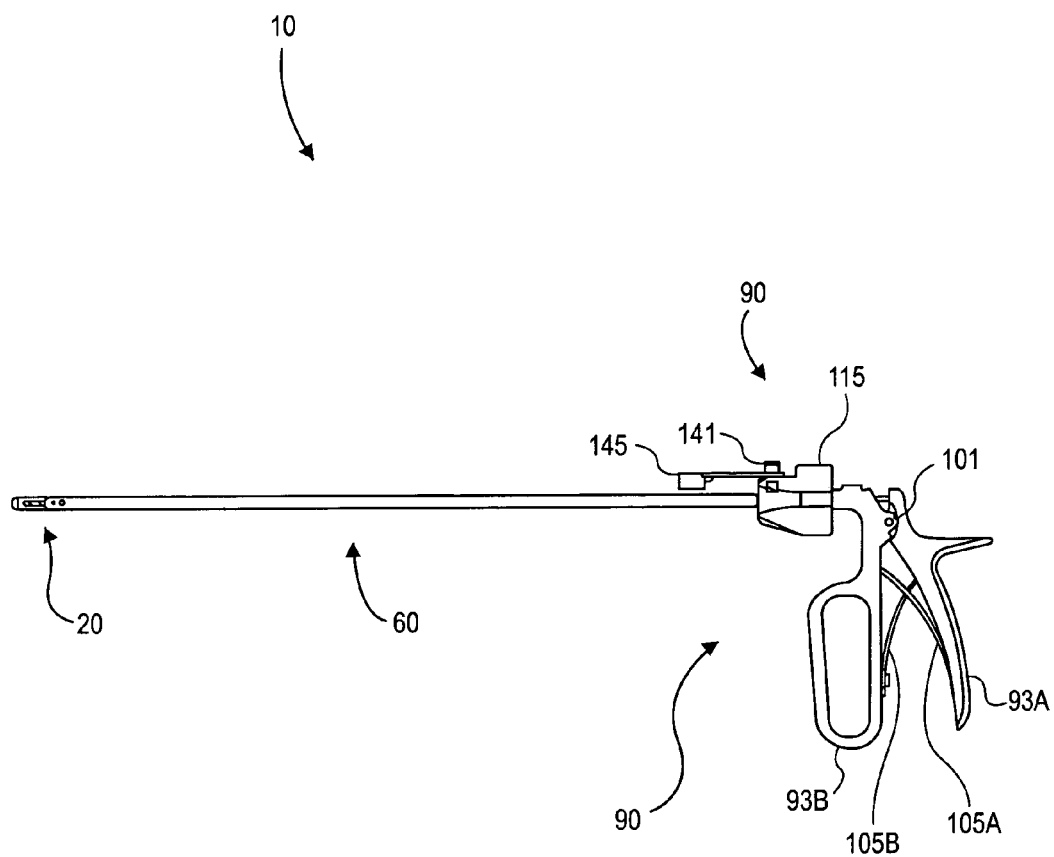
FIG. 1B is a side elevation view of the clip removing apparatus illustrated in FIG. 1A.

Referring now to FIGS. 1A and 1B, an endoscopic clip removal apparatus, generally designated 10, is illustrated in accordance with the invention. Generally, apparatus 10 comprises a gripping or clip-engagement assembly, generally designated 20; an elongate endoscopic shaft assembly, generally designated 60; and an actuator assembly, generally designated 90. Gripping assembly 20 is alternately movable between an open state (see FIG. 2A) and a closed state (see FIG. 2B), and is adapted for manipulating a surgical clip. An example of a suitable clip is described below and illustrated in FIG. 7. Actuator assembly 90 enables the manual actuation necessary for opening and closing gripping assembly 20, and thus is mechanically referenced to gripping assembly 20 through shaft assembly 60 as described in more detail below.

Apparatus 10 is particularly designed for use in endoscopic surgical procedures. In general terms, an endoscopic procedure involves first creating a surgical port at a designated surgical site, i.e., on a patient's body, to provide access into the body cavity. Thereafter, a surgical instrument (e.g., apparatus 10) selected as appropriate for the procedure is inserted into the body cavity through the surgical port, manipulated in accordance with the procedure, and then removed from the body cavity back through the surgical port. Thus, shaft assembly 60 of apparatus 10 should be long enough to reach the intended location within the body cavity, while permitting actuator assembly 90 to be comfortably handled by the surgeon from outside of the body cavity. The length of shaft assembly 60 typically ranges from approximately 30 cm to approximately 35 cm. In addition, the respective overall outer diameters of gripping assembly 20 (when in the closed state) and shaft assembly 60 should be at least slightly less than the inside diameter of the surgical port. As two examples, 5-mm and 10-mm surgical ports are commonly created in the course of endoscopic procedures.

Figure 2A:
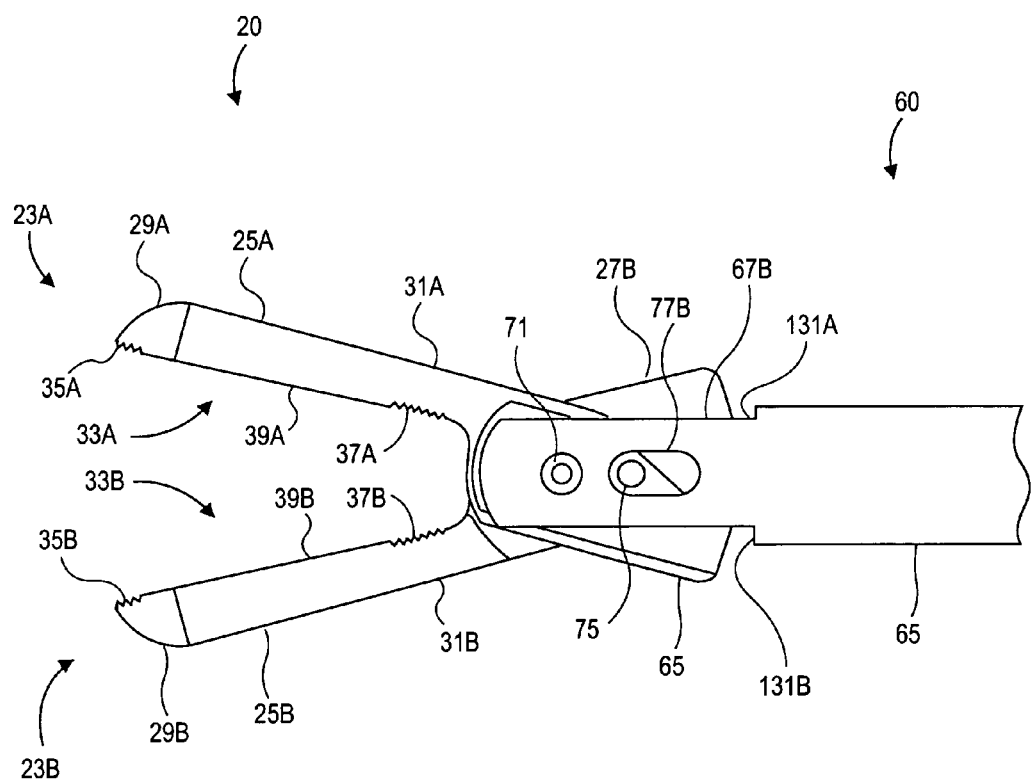
FIG. 2A is a side elevation view of a gripping assembly provided with the apparatus illustrated in FIG. 1A, wherein the gripping assembly is in an open state.
Figure 2B:
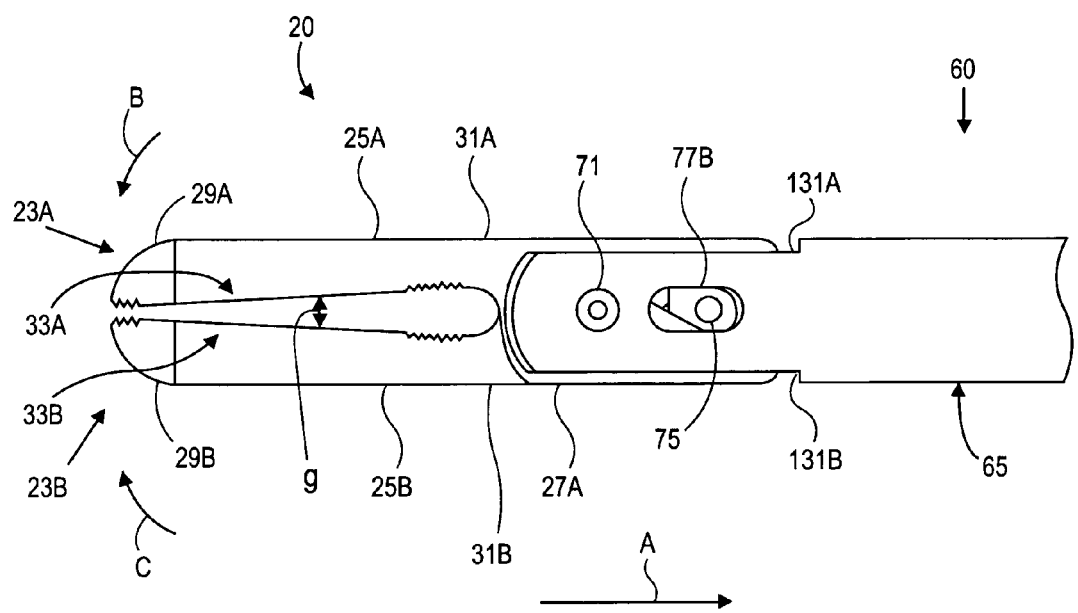
FIG. 2B is a side elevation view of the gripping assembly illustrated in FIG. 2A, wherein the gripping assembly is in a closed state.
Figure 3:
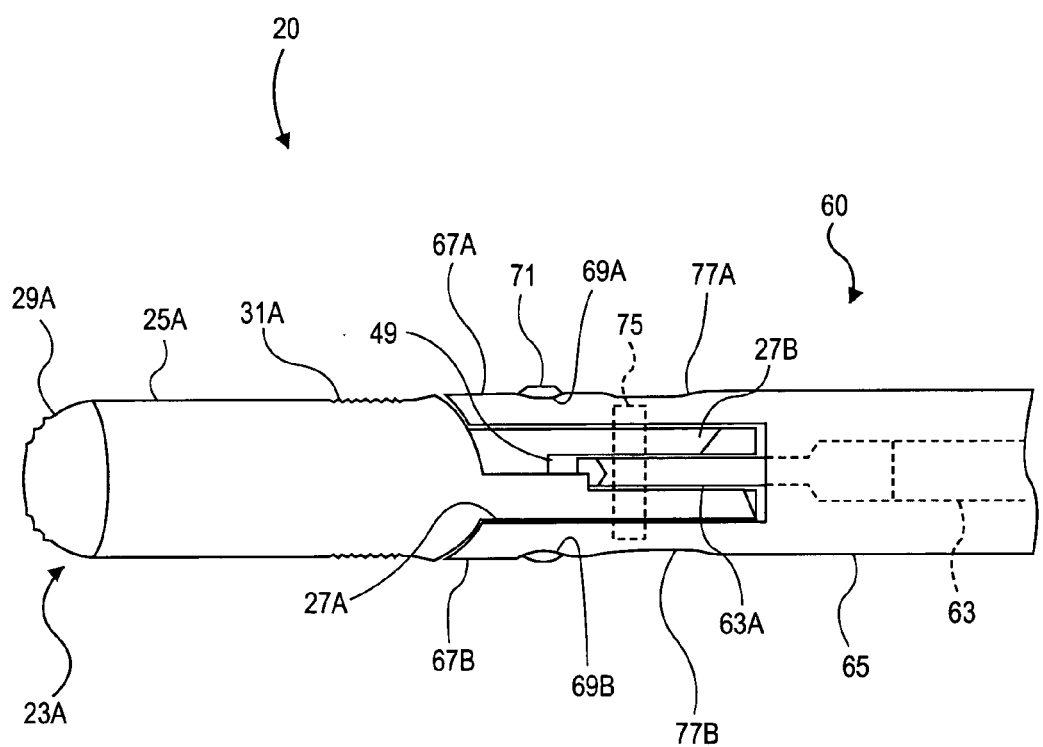
FIG. 3 is a top or bottom plan view of the gripping assembly illustrated in FIGS. 2A and 2B.
Figure 4:
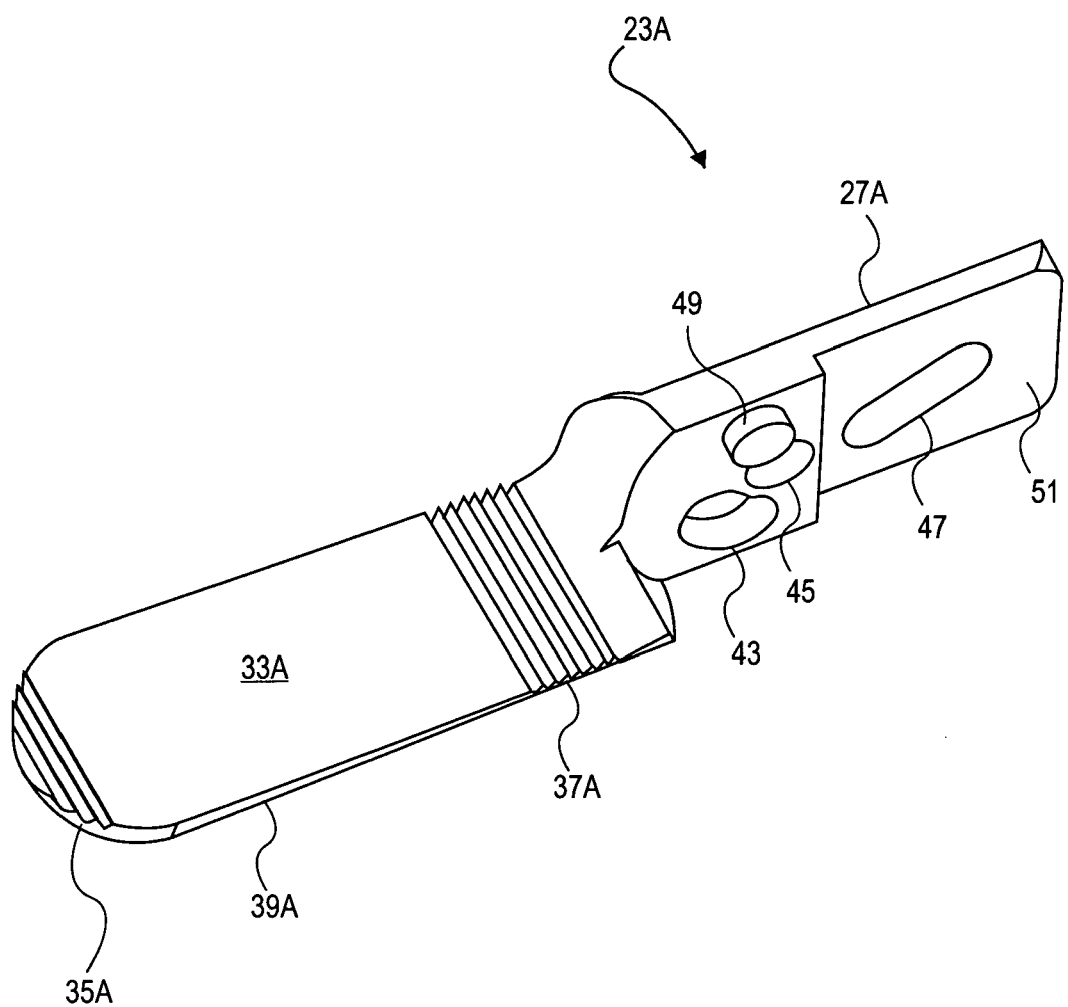
FIG. 4 is a perspective view of a jaw member provided with the gripping assembly illustrated in FIGS. 2A and 2B.

Referring now to FIGS. 2A–4, gripping assembly 20 and a portion of shaft assembly 60 are illustrated in more detail. FIG. 2A illustrates gripping assembly 20 in its open state, while FIG. 2B illustrates gripping assembly 20 in its closed state. Referring primarily to FIGS. 2A, 2B and 4, gripping assembly 20 comprises a pair of opposing first and second jaws, generally designated 23A and 23B, respectively. Each jaw 23A and 23B respectively comprises a gripping region 25A and 25B and a base region 27A and 27B. Each gripping region 25A and 25B respectively comprises a distal end region 29A and 29B, a proximal end region 31A and 31B, and an inside surface, generally designated 33A and 33B. Each inside surface 33A and 33B extends from its respective distal end region 29A and 29B to proximal end region 31A and 31B. As best shown in FIG. 2B, in which gripping assembly 20 is in its fully closed state, a jaw gap g is defined between inside surfaces 33A and 33B along the respective lengths of gripping regions 25A and 25B. Jaw gap g exists between respective distal end regions 29A and 29B of gripping regions 25A and 25B, even at the fully closed state shown in FIG. 2B. Thus, in the preferred use of apparatus 10, first and second jaws 23A and 23B of gripping assembly 20 never close completely and their respective inside surfaces 33A and 33B never contact each other. This feature prevents tissue trauma that might otherwise occur from inadvertent or mistaken actuation of apparatus 10 during use. Moreover, along at least a portion of the length of each inside surface 33A and 33B, each inside surface 33A and 33B tapers outwardly in the direction from its respective distal end region 29A and 29B to proximal end region 31A and 31B. Thus, jaw gap g increases along this direction from a minimum distance at or near distal end regions 29A and 29B to a maximum distance at or near proximal end regions 31A and 31B. From the perspective of FIG. 2B, the profile of jaw gap g could be characterized as being substantially teardrop-shaped. As one example, the distance of jaw gap g increases from approximately 0.020 inches to approximately 0.075 inches in the proximal direction.

In addition, as specifically shown in FIGS. 2A and 4, each inside surface 33A and 33B respectively comprises a distally located rough or high-friction region 35A and 35B, a proximally located rough or high-friction region 37A and 37B, and a smooth or low-friction region 39A and 39B between distal rough region 35A and 35B and proximal rough region 37A and 37B. It will be noted that FIG. 4 illustrates the detailed structure of first jaw 23A only, with the understanding that second jaw 23B is symmetrically structured. Each rough region 35A, 35B, 37A and 37B is structured, coated and/or treated in any suitable manner to create areas of high friction on its respective inside surface 33A and 33B, but without adversely affecting or reacting with any tissue coming into contact with first and second jaws 23A and 23B. Preferably, each rough region 35A, 35B, 37A and 37B is defined by grooves, teeth, corrugations, or serrations on its respective inside surface 33A and 33B as shown in FIGS. 2A and 4. Each smooth region 39A and 39B is structured, coated and/or treated in any suitable manner to create an area of low friction on its respective inside surface 33A and 33B, again without adversely affecting any tissue coming into contact with first and second jaws 23A and 23B. Preferably, smooth regions 39A and 39B are provided by polishing inside surfaces 33A and 33B in accordance with a suitable metal polishing process. These features of first and second jaws 23A and 23B enhance control over the clip being manipulated by apparatus 10, as described below.

As best shown in FIG. 4, in which the structural details of first jaw 23A are shown with the understanding that second jaw 23B is similarly structured, each respective base section 27A and 27B has a pivot pin-receiving aperture or slot 45, a boss-receiving aperture or slot 43, and an actuator pin-receiving aperture or slot 47. Apertures 43, 45 and 47 are formed through base section 27A and 27B generally transversely to the axis of shaft assembly 60. A boss 49 extends transversely from an inside surface 51 of base section 27A and 27B. In the assembly of first and second jaws 23A and 23B together such as shown in FIG. 3, boss 49 of first jaw 23A is inserted into boss-receiving aperture 43 of second jaw 23B, and boss 49 of second jaw 23B is inserted into boss-receiving aperture 43 of first jaw 23A. Each boss 49 is rotatably supported in its corresponding boss-receiving aperture 43 to assist in keeping first jaw 23A and second jaw 23B properly aligned during movement.

Figure 5:
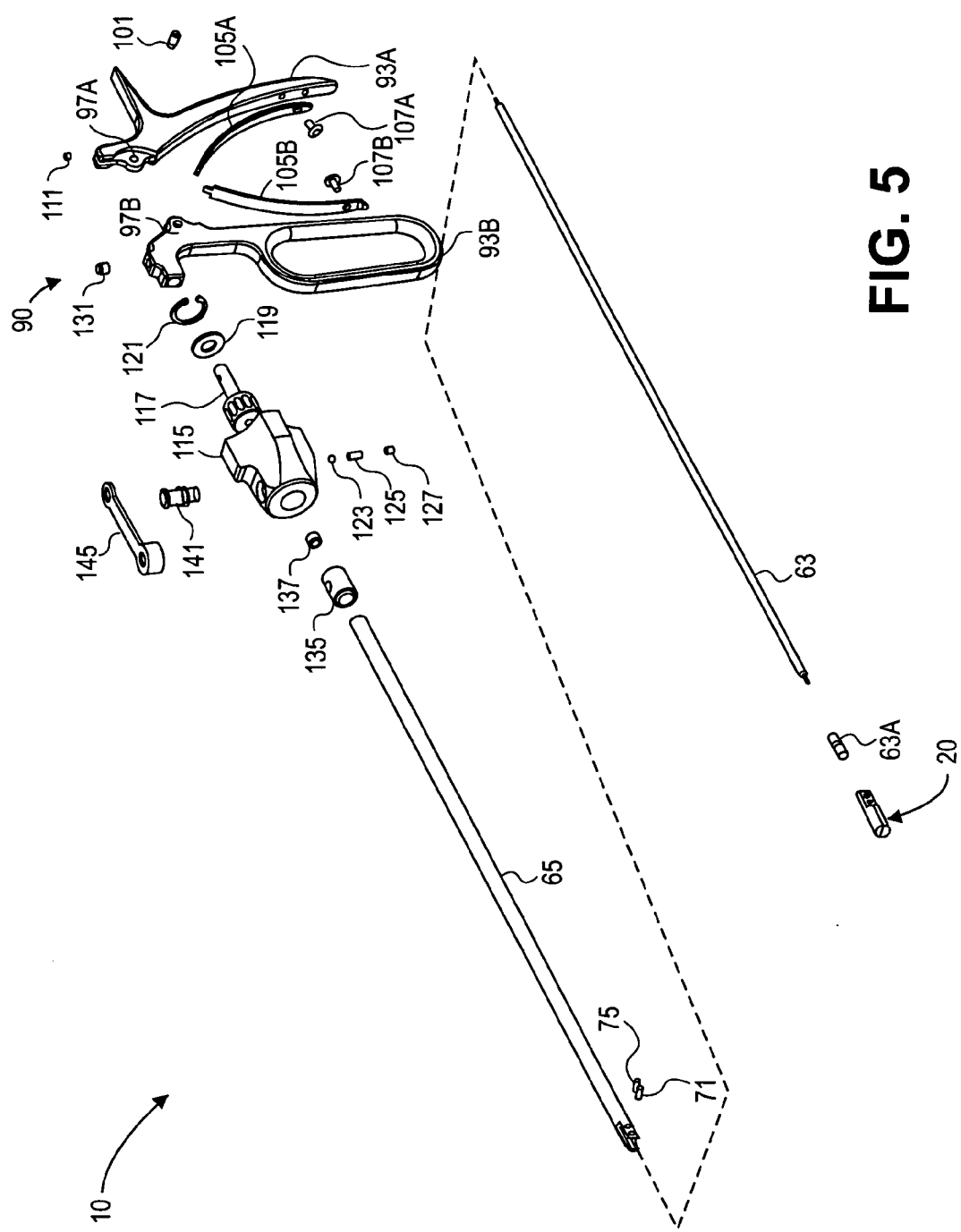
FIG. 5 is a perspective exploded view of the clip removing apparatus illustrated in FIGS. 1A and 1B.

As shown in FIGS. 3 and 5, shaft assembly 60 preferably comprises a centrally disposed elongate member such as rod 63 and a hollow elongate member such as a sleeve 65 coaxially disposed around rod 63. Inside surface 51 (see FIG. 4) of each jaw 23A and 23B has a stepped profile so that, when first and second jaws 23A and 23B are assembled together, a transverse gap exists into which rod 63 or a distal end piece 63A thereof is inserted as shown in FIG. 3. As also shown in FIG. 3, at the distal end of shaft assembly 60, sleeve 65 comprises a cut-out section defining two or more sleeve extensions 67A and 67B. In assembling apparatus 10, first and second jaws 23A and 23B are assembled together as described above and then inserted into the distal end of shaft assembly 60. First and second jaws 23A and 23B are inserted to a point at which pivot pin-receiving apertures 45 (see FIG. 4) are aligned with corresponding sleeve apertures 69A and 69B formed through sleeve extensions 67A and 67B, respectively. A suitable pivot pin 71 (e.g., a rivet) is then inserted through sleeve apertures 69A and 69B and pivot pin-receiving apertures 45 and secured by conventional means. In the assembled form, first jaw 23A and second jaw 23B rotate about pivot pin 71 in opposite senses to enable gripping assembly 20 to be actuated between the open state (FIG. 2A) and the closed state (FIG. 2B) in a scissors-like fashion.

As shown in FIGS. 2A, 2B and 3, shaft assembly 60 further comprises an actuator pin 75 transversely disposed through rod 63 near the distal end thereof, and sleeve extensions 67A and 67B comprise sleeve slots 77A and 77B, respectively. In assembling apparatus 10, actuator pin 75 is inserted through respective actuator pin-receiving apertures 47 (see FIG. 4) of first and second jaws 23A and 23B (see FIG. 4) as well as through sleeve slots 77A and 77B. The movement of actuator pin 75 within actuator pin-receiving apertures 47 and sleeve slots 77A and 77B is effected by actuator assembly 90 through the interconnection of rod 63 and actuator assembly 90 (see FIGS. 5 and 6). The configuration of actuator pin-receiving apertures 47 and sleeve slots 77A and 77B, and their positions relative to each other and to actuator pin 75 after assembly of apparatus 10, enable gripping assembly 20 to move from the open position shown in FIG. 2A to the closed position shown in FIG. 2B as a result of the linear actuation of rod 63 by actuator assembly 90. For instance, in the embodiment illustrated in FIG. 4, actuator pin-receiving aperture 47 is oriented obliquely with respect to the longitudinal axis along which rod 63 is actuated. In FIG. 2A, the forward or distal position of actuator pin 75 in relation to sleeve slots 77A and 77B is associated with the open state of gripping assembly 20. In FIG. 2B, the retracted or proximal position of actuator pin 75 in relation to sleeve slots 77A and 77B is associated with the closed state of gripping assembly 20. That is, retraction of rod 63 (see, e.g., FIG. 3) in direction indicated by arrow A in FIG. 2B causes actuator pin 75 to bear against the obliquely oriented inside surfaces of actuator pin-receiving apertures 47 (see FIG. 4), thereby causing first jaw 23A and second jaw 23B to rotate to the closed state as indicated by arrows B and C, respectively.

Figure 5A:
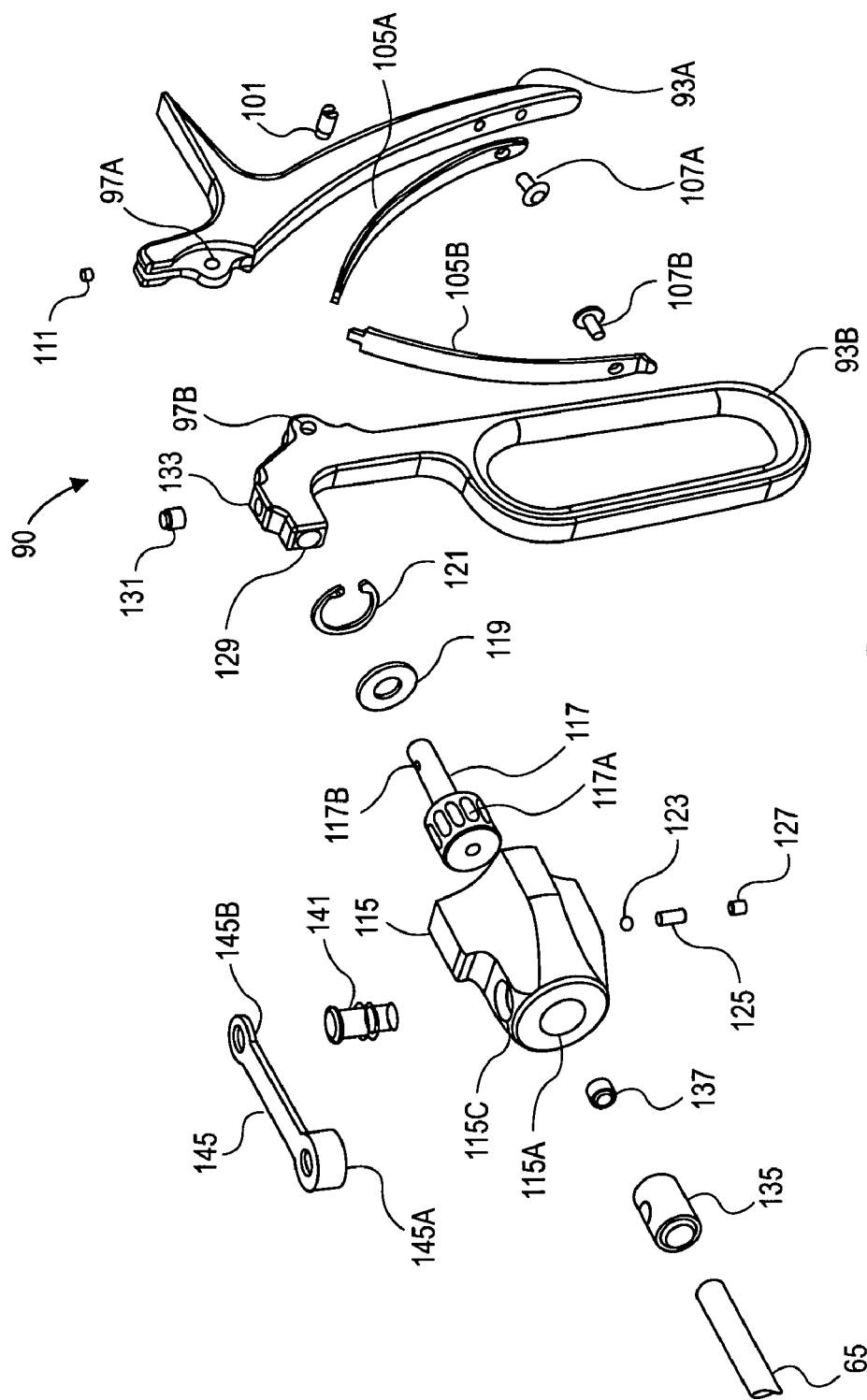
FIG. 5A is a detailed perspective exploded view of an actuation assembly provided with the clip removing apparatus.

Referring now to the exploded views of FIGS. 5 and 5A, the various components of apparatus 10 according to a preferred embodiment are illustrated prior to the completed assembly of apparatus 10 illustrated in FIGS. 1A and 1B. In this embodiment, actuator assembly 90 is designed for manual actuation by the surgeon. Actuator assembly 90 comprises a two-piece handle that includes a first handle portion 93A and a second handle portion 93B connected together at respective pivot locations 97A and 97B with a suitable pin or fastening element 101. A pair of arcuate spring elements 105A and 105B contact each other at their upper ends between first and second handle portions 93A and 93B, and are connected to first and second handle portions 93A and 93B using respective fastening elements 107A and 107B. As a result, first handle portion 93A is biased away from second handle portion 93B. Rod 63 of shaft assembly 60 is inserted through sleeve 65 to interconnect gripping assembly 20 with actuator assembly 90. Preferably, rod 63 mechanically communicates with first handle portion 93A by providing rod 63 with a ball-shaped proximal end 63B that is inserted into a socket 109 formed in first handle portion 93A (see FIG. 6). Socket 109 can be sealed with a suitable plug 111. It can thus be seen that upon squeezing handle portions 93A and 93B toward each other, first handle portion 93A retracts rod 63 and actuator pin 75 to the position shown in FIG. 2B to move gripper assembly 20 to its closed state, whereby a clip can be grasped and manipulated as appropriate to the procedure being performed.

Figure 6:
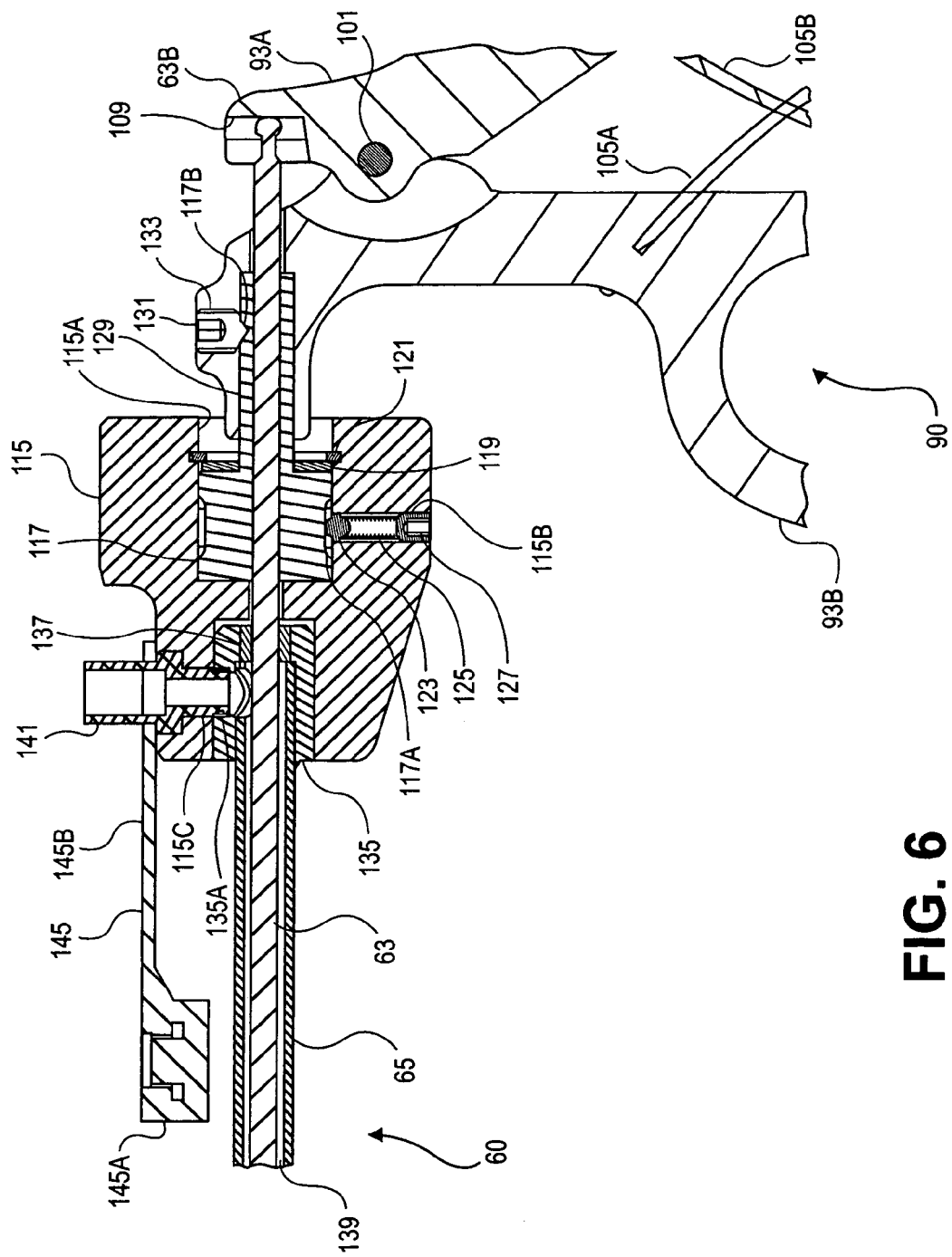
FIG. 6 is a cross-sectional, partially cutaway side elevation view of the interfacial region between a shaft assembly and the actuator assembly of the clip removing apparatus.

Referring to FIGS. 5, 5A and 6, sleeve 65 of shaft assembly 60 is attached to actuator assembly 90 so as to enable sleeve 65 to be rotated 360 degrees about the longitudinal axis of shaft assembly 60. Because sleeve 65 is affixed to gripper assembly 20 as described above with reference to FIGS. 2A, 2B and 3, rotation of sleeve 65 likewise causes rotation of gripper assembly 20. As described below, this rotation can be accomplished while gripper assembly 20 is within a body cavity at a surgical site, and thus can be useful in performing appropriate manipulations.

Continuing with FIGS. 5, 5A and 6, to facilitate rotation of sleeve 65, sleeve 65 is preferably attached to a knob 115 or similar component adapted for manipulation by the user. In the preferred configuration, knob 115 is rotatably attached to a barrel element 117. Barrel element 117 is retained within an axial bore 115A of knob 115 by a washer 119 and C-clip 121. A number of elongate recesses 117A are formed around the circumference of barrel element 117. To provide a rotational indexing action for shaft assembly 60 with respect to actuator assembly 90, each elongate recess 117A sequentially interacts with a spring-loaded ball bearing assembly transversely disposed in a radial bore 115B of knob 115. The spring-loaded ball bearing assembly comprises a ball 123, a spring 125, and a retaining element 127. Ball 123 is biased by spring 125 into a selected elongate recess 117A to define a given index position. Knob 115 is indexed to the next position (either clockwise of counterclockwise) by rotating knob 115 in relation to stationary barrel element 117, which causes ball 123 to roll over barrel element 117 and into the next elongate recess 117A. Barrel element 117 is inserted into an axial bore 129 of second handle portion 93B of actuator assembly 90. As shown in FIG. 6, barrel element 117 is fixedly secured within bore 129 of second handle portion 93B by inserting a radial element 131 having a pointed tip through a radial bore 133 of second handle portion 93B until the pointed tip engages a depression 117B in barrel element 117. By this configuration, knob 115 and shaft assembly 60 can be rotated in an indexing fashion with respect to barrel element 117 and first and second handle portions 93A and 93B of actuator assembly 90.

As best shown in the cross-sectional view of FIG. 6, shaft assembly 60 is mechanically referenced to actuator assembly 90 by connecting rod 63 to first handle portion 93A as described above, and further by inserting sleeve 65 and/or a collar 135 coaxial with sleeve 65 into the distal section of axial knob bore 115A. Sleeve 65 is secured to collar 135 such as by press-fitting or welding. An annular spacer or seal member 137 is disposed at the proximal end of sleeve 65, and is coaxially interposed between collar 135 and rod 63. It can be seen that in connecting with first handle portion 93A, rod 63 extends through sleeve 65, axial knob bore 115A, barrel element 117, and second handle portion 93B.

It can be further seen in FIG. 6 that, upon assembly of apparatus 10, an annular passage 139 is defined between the inner surface of sleeve 65 and the outer surface of rod 63. Annular passage 139 provides a fluid passage that traverses the length of shaft assembly 60 and terminates at outlets located at or near the interface between shaft assembly 60 and gripper assembly 20, such as outlets 131A and 131B indicated in FIGS. 2A and 2B. In the preferred embodiment illustrated in FIGS. 5, 5A and 6, another radially disposed bore 115C formed through knob 115 serves as the fluid inlet into annular passage 139. A fitting 141 is mated to radial bore 115C and extends through a bore 135A in collar 135 to accommodate the connection of a suitable fluid supply source, such as a syringe and/or tubing, to annular passage 139 of shaft assembly 60. Fitting 141 can also be employed to retain collar 135 and sleeve 65 within axial knob bore 115A. After using apparatus 10, the user can flush apparatus 10 with a suitable flushing fluid such as deionized water and clean any gross debris residing on the components of gripper assembly 20. A resilient closure element 145 is connected to fitting 141 to close the fluid inlet during non-use of the flushing system. Preferably, closure element 145 comprises a cap 145A and a strap 145B. Strap 145B is annularly attached to fitting 141 to conveniently retain closure element 145 with apparatus 10 when not in use. To close fitting 141, strap 145B is folded over and cap 145A pressed onto fitting 141.

Figure 7:
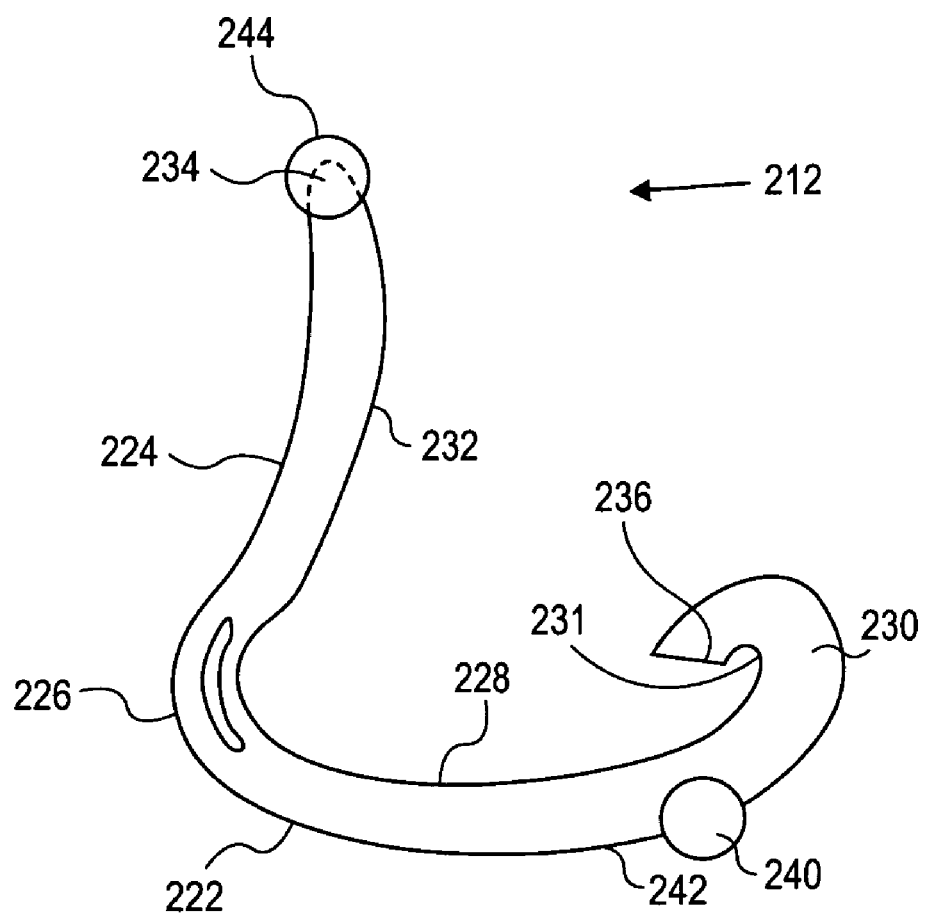
FIG. 7 is a side elevation view of one example of a surgical clip that can be manipulated by the clip removing apparatus of the present invention.

As indicated previously, apparatus 10 is particularly useful for removing a hemostatic clip that has been previously latched around a vessel or other type of tissue to ligate the vessel and thereby stop or reduce the flow of fluid through the vessel. Referring now to FIG. 7, a hemostatic clip, generally designated 212, is illustrated as one example of a clip suitable for manipulation by apparatus 10. Clip 212 can be constructed from any suitable biocompatible material, such as certain metals and polymers. In the particular embodiment represented in FIG. 6, clip 212 comprises a one-piece integral polymeric body formed of a suitable strong biocompatible engineering plastic of the type commonly used for surgical implants. Suitable examples include polyethylene terephthalate (PET), polybutylene terephthalate (PBT) polyoxymethylene, or other thermoplastic materials having similar properties that can be injection-molded, extruded or otherwise processed into like articles. Similar clips are described in detail in commonly assigned U.S. Pat. No. 4,834,096 to Oh et al. and U.S. Pat. No. 5,062,846 to Oh et al., the disclosures of which are incorporated herein in their entireties.

Figure 8A:
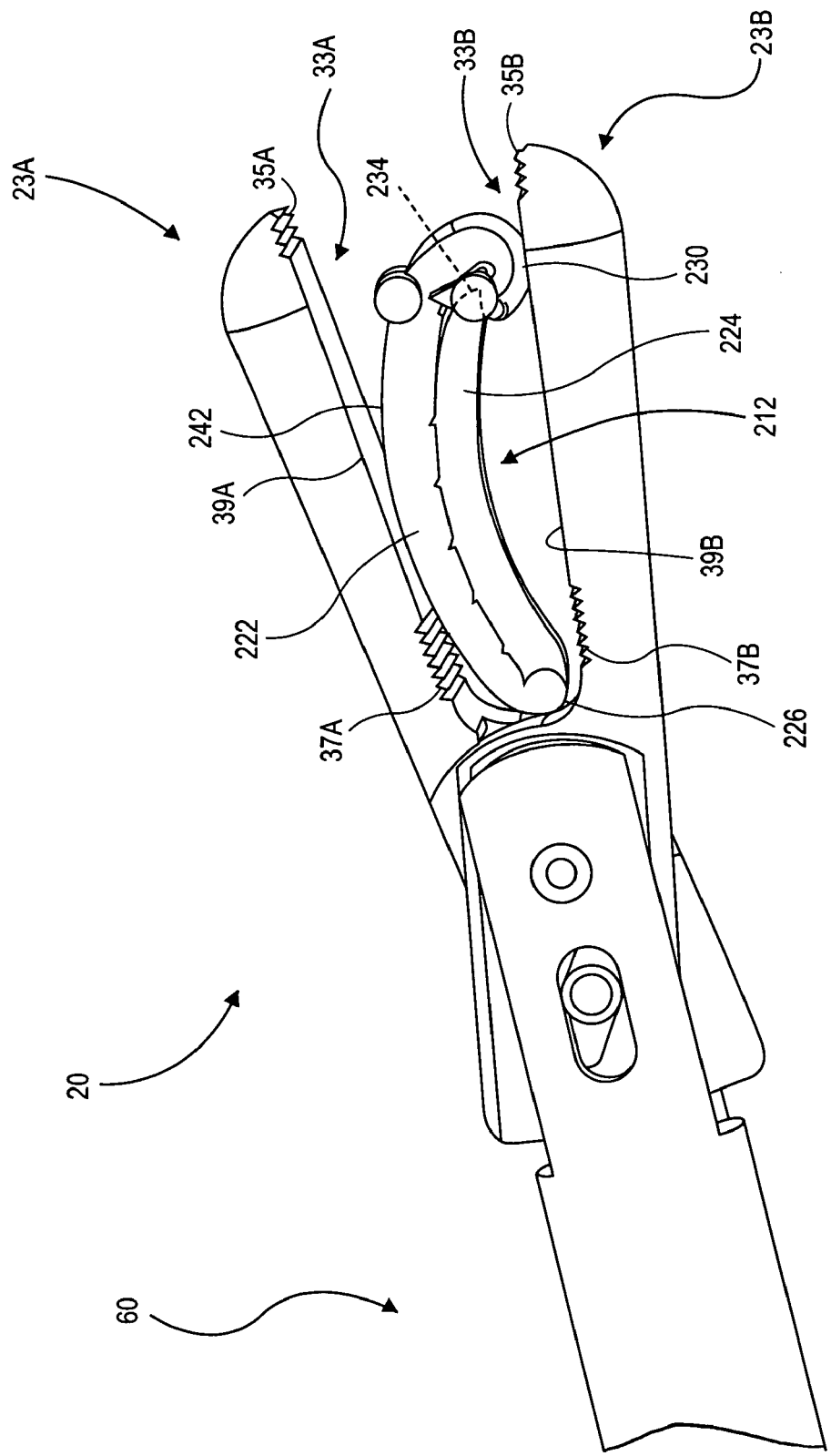
FIGS. 8A–8E are sequential side elevation views illustrating the gripping assembly of the clip removing apparatus engaging, unlatching, and extracting a surgical clip from a surgical site in accordance with a method of the present invention.

The body of clip 212 comprises a first or outer leg 222 and a second or inner leg 224 joined at their proximal ends by an integral hinge section 226. Outer leg 222 has a concave inner surface 228 transitioning to a curved, C-shaped hook section 230 at its distal end defining a latching recess 231. Inner leg 224 has a convex inner surface 232 that is complementary to concave inner surface 228 in the closed or latched position of clip 212, which is shown in FIG. 8A. Thus, a vessel around which clip 212 is applied can be completely occluded in use. Inner leg 224 has a pointed tip 234 at its distal end. As such, convex inner surface 232 of inner leg 224 and concave inner surface 228 of outer leg 222 have substantially matching radii of curvature. Hook section 230 is distally reversely curved inwardly, and has a transverse beveled surface 236. Beveled surface 236 and concave inner surface 228 define recess 231, which is adapted for conformally engaging tip 234 in the latched condition of clip 212. Adjacent the distal end of the outer leg 222 and immediately inwardly of hook section 230, a pair of cylindrical bosses 240 are formed coaxially on the opposed lateral surfaces of outer leg 222. Bosses 240 project outwardly beyond convex outer surface 242 of outer leg 222. At the distal end of inner leg 224, a pair of cylindrical bosses 244 are formed coaxially on opposed lateral surfaces of inner leg 224 at the tip 234, and extend longitudinally forwardly beyond tip 234.

In the use of clip 212, bosses 240 and 244 are engaged by an appropriate clip applicator instrument, such as the type described in the aforementioned U.S. Pat. No. 5,100,416, and are pivoted inwardly thereby about hinge section 226 to engage tip 234 at the end surface of hook section 230. Further pivotal movement of the applicator instrument longitudinally elongates outer leg 222 and deflects hook section 230, allowing tip 234 to align with recess 231. Upon release of the applicator instrument, tip 234 snaps into and is conformably seated in recess 231, at a latched condition shown in FIG. 8A. In the latched condition, tip 234 is engaged between concave inner surface 228 and beveled surface 236, thereby securely clamping a designated vessel or other tissue between concave inner surface 228 and convex inner surface 232.

Another example of a particularly suitable clip is the HEM-O-LOK® clip commercially available from the assignee of the present invention. These clips are currently available in sizes designated "M", "ML", and "L". Apparatus 10 of the present invention is capable of handling all three sizes of HEM-O-LOK® clips.

Referring now to FIGS. 8A–8E, an example of the operation of apparatus 10 will now be described, in which apparatus 10 is used to unlatch a clip and remove the clip from a surgical site. In describing the operation of apparatus, clip 212 just described with reference to FIG. 7 will be referred to for illustrative purposes. Also for illustrative purposes, it will be assumed that clip 212 initially resides within a body cavity in its latched condition in ligating relation to a vessel or other tissue, and an appropriate surgical port has been created through the patient's body (such as by using a trocar) to provide access to the internal site of the ligature.

In the operation of apparatus 10, the surgeon or other user squeezes first and second handles 93A and 93B (see FIGS. 1A and 1B) to actuate gripper assembly 20 of apparatus 10 into its closed state shown in FIG. 2B, and then inserts closed gripper assembly 20 through the surgical port to the surgical site where clip 212 is located in the latched condition. Once gripper assembly 20 reaches the surgical site, the surgeon then releases the applied squeezing force on handle portions 93A and 93B, allowing spring elements 105A and 105B (see FIGS. 1A and 1B) to bias handle portions 93A and 93B outwardly and gripper assembly 20 to return to the open state shown in FIG. 2A. As shown in FIG. 8A, the surgeon then longitudinally aligns gripper assembly 20 into engagement with clip 212 such that smooth region 39A of first inside surface 33A contacts outer convex surface 242 of first leg 222 of clip 212, smooth region 39B of second inside surface 33B contacts hook section 230, and proximal rough region 37B of second inside surface 33B contacts hinge section 226. Partial actuation of gripper section 20 may be necessary to effect the contact and alignment with clip 212. The alignment allows the surgeon to have complete control over clip 212 throughout the remaining steps of the clip removal procedure. It will be noted that gripper assembly 20 is symmetrically structured, such that the respective positions of first and second jaws 23A and 23B in relation to clip 212 could be reversed.

With gripping assembly 20 properly aligned in engagement with clip 212, the surgeon then begins to squeeze handle portions 93A and 93B (see FIGS. 1A and 1B). This causes first and second jaws 23A and 23B to move toward each other and hence toward the closed state, thereby bearing on first and second legs 222 and 224 of clip 212 to compress clip 212. As gripping assembly 20 compresses clip 212, first leg 222 begins to straighten or flatten out. While first leg 222 is being straightened, hook section 230 is free to move forwardly toward the distal end of gripping assembly 20 and pivot outwardly. Smooth surfaces 39A and 39B facilitate the straightening of first leg 222 and the concomitant movement and pivoting of hook section 230, as first leg 222 and hook section 230 are permitted to slide along smooth surfaces 39A and 39B, respectively. Moreover, smooth surfaces 39A and 39B prevent gripping assembly 20 from crushing or otherwise damaging clip 212. At the same time, however, proximal rough region 37B of second inside surface 33B maintains contact with hinge section 226 of clip 212. The retention of hinge section 226 on proximal rough region 37B prevents significant movement of hinge section 226 during compression, thereby defeating the tendency of clip 212 to jump out or otherwise become disengaged from gripper assembly 20. Other than the restriction on hinge section 226, second leg 224 is unrestrained, and thus first leg 222 could be characterized as lengthening, straightening, or otherwise moving with respect to second leg 224 during compression of clip 212.

Figure 8B:
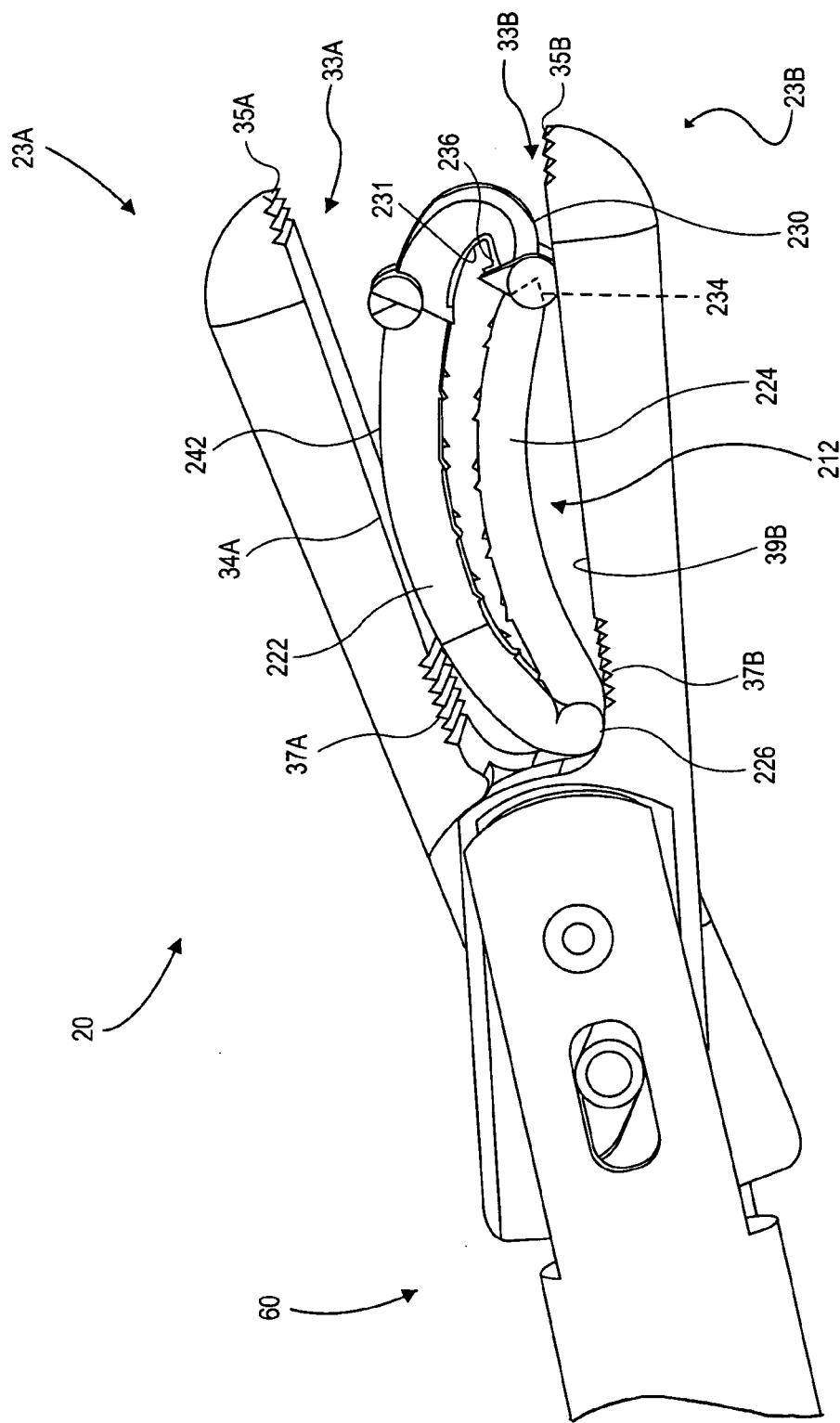
Figure 8C:
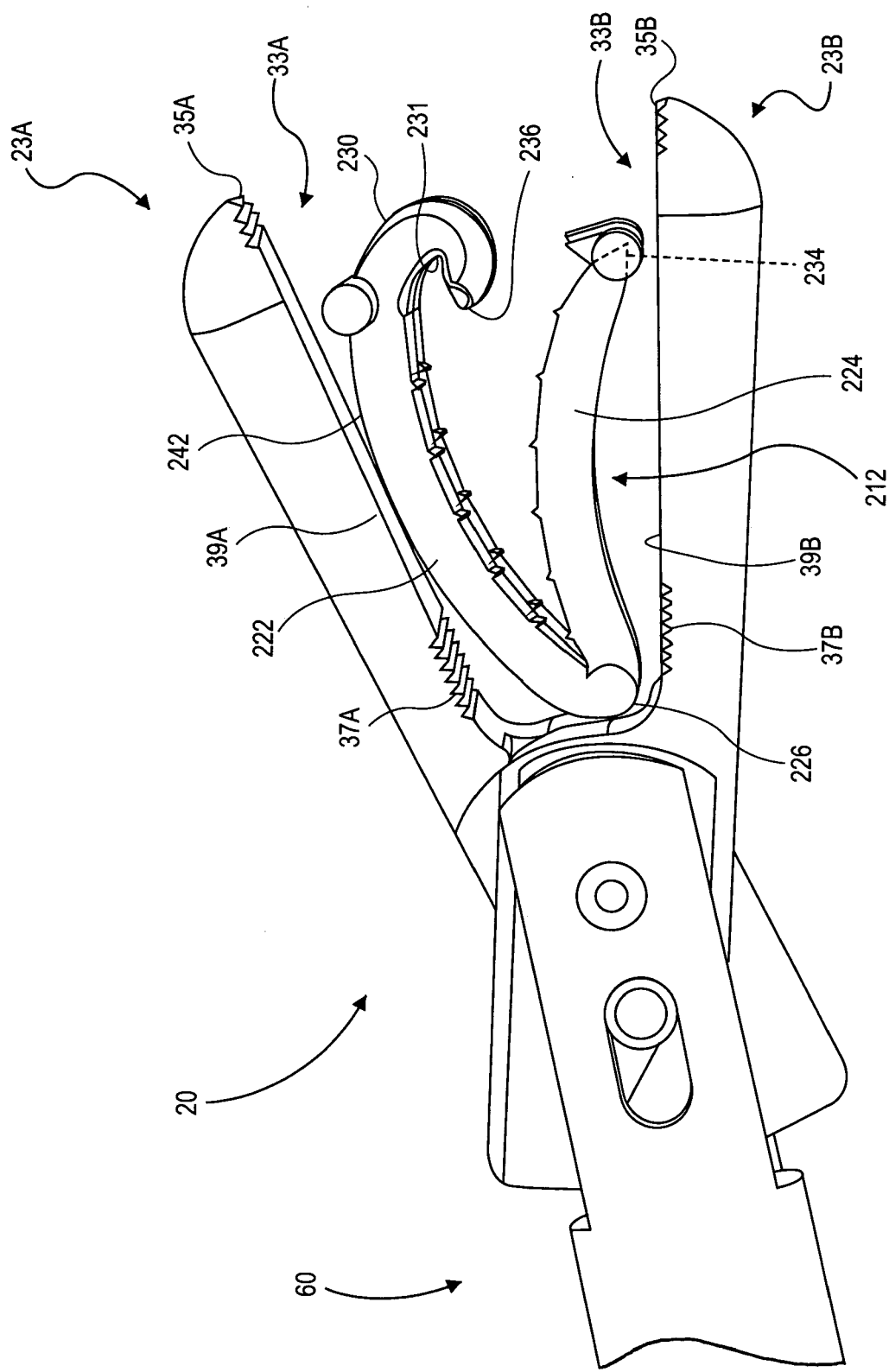

The compression of clip 212 and concomitant yielding or deformation of hook section 230 in effect causes tip 234 of second leg 224 to be progressively withdrawn from recess 231 of hook section 230. As shown in FIG. 8B, tip 234 eventually clears beveled surface 236 and deflects to its unlatched condition under the inherent biasing of the compressed clip configuration. Upon further release, clip 212 begins to assume the fully open, unlatched condition shown in FIG. 8C.

Figure 8D:
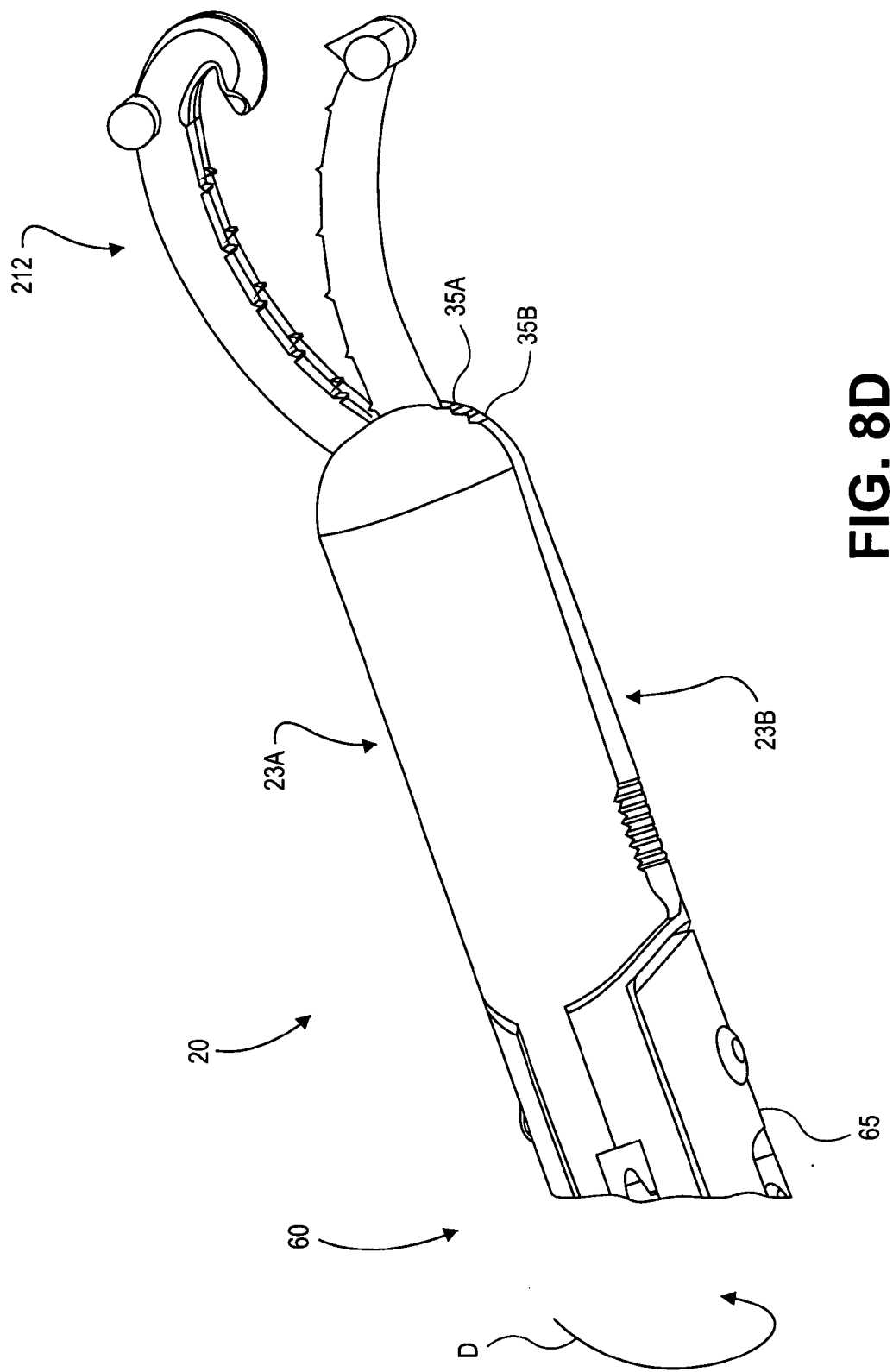
Figure 8E:
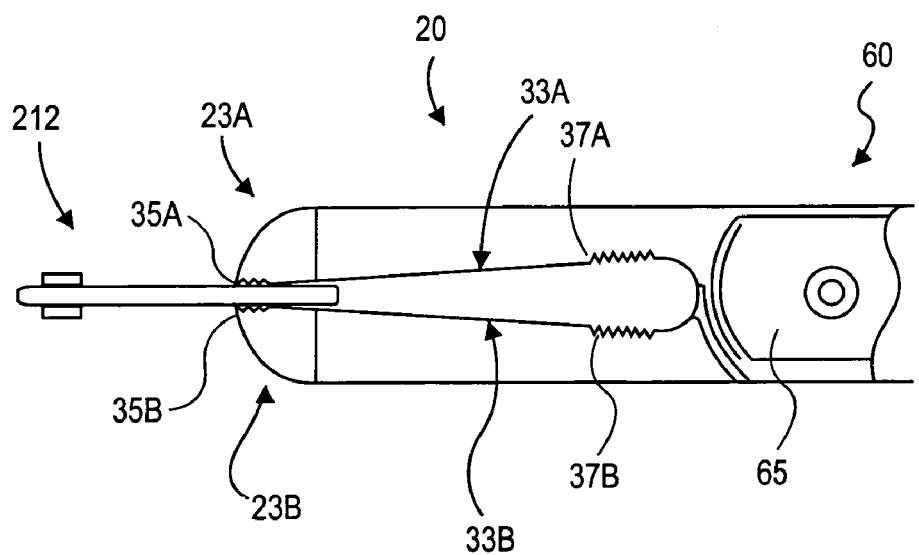

At this point, apparatus 10 can be withdrawn from the surgical site. Conventionally, a separate instrument is utilized to retrieve clip 212 and remove it from the surgical site, through the trocar cannula and surgical port, and out from the patient's body. In accordance with an aspect of the present invention, however, apparatus 10 can also advantageously be used to extract clip 212 from the patient's body, thereby eliminating the need for a separate retrieval instrument. As shown in FIGS. 8D and 8E, this is preferably accomplished by rotating sleeve 65 of shaft assembly 60, and consequently gripper assembly 20, 90 degrees or thereabouts as indicated by arrow D, so that first and second jaws 23A and 23B of gripper assembly 20 can be actuated into grasping the lateral surfaces of clip 212. The respective distal rough regions 35A and 35B of first and second inside surfaces 33A and 33B of first and second jaws 23A and 23B facilitate the grasping of clip 212 in this manner, as well as enhance the user's control over clip 212 during the subsequent extraction of clip 212 from the body cavity.

It can therefore be seen from the foregoing description that the present invention provides an apparatus and method for removing a clip that has been attached to a vessel or other tissue for ligating purposes. The apparatus is capable of removing the clip by both unlatching the clip as well as subsequently grasping the clip in order to remove the clip from the surgical site. The apparatus is particularly adapted for endoscopic procedures. The structure of the apparatus enables improved control over manipulation of the clip by the user thereof. The apparatus is structured so as to ensure that the clip does not escape the jaws of the apparatus during compression of the clip, and that the clip does not become misaligned or damaged. The apparatus is further structured so as to prevent damage to the vessel or other tissue while the clip is being manipulated.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for unlatching a clip initially provided in a latched state, the clip comprising first and second legs joined at a hinge region of the clip, the first and second legs having respective distal end members that, in the latched state, are engaged with each other to define an interlocked clip region, the method comprising the steps of:
    (a) providing first and second jaws pivotably connected to each other and movable between an open position and a closed position, the first jaw comprising a first distal jaw end, a first proximal jaw end, and a first inside surface extending between the first distal jaw end and first proximal jaw end, and the second jaw comprising a second distal jaw end, a second proximal jaw end, and a second inside surface extending between the second distal jaw end and second proximal jaw end, wherein at the closed position, the inside surfaces define a jaw gap therebetween, and at least a portion of the jaw gap increases in distance along a direction from the respective distal jaw ends toward the proximal jaw ends;
    (b) engaging the clip with the first and second jaws by bringing the first jaw into contact with the first leg of the clip and the second jaw into contact with the interlocked clip region and hinge region, with the hinge region disposed near the second proximal jaw end; and
    (c) compressing the clip by moving the first and second jaws toward their closed position, whereby the respective distal end members of the first and second legs of the clip become separated.

2. The method according to claim 1 wherein the first and second legs of the clip are arcuate, and a concave inside surface of the first leg faces a convex inside surface of the second leg.

3. The method according to claim 2 wherein the clip is constructed from a polymeric material.

4. The method according to claim 1 wherein the distal end member of the first leg of the clip comprises a hook region, the distal end member of the second leg is retained by the hook region to define the interlocked clip region in the latched state of the clip, and the second jaw contacts the hook region during the clip engaging step.

5. The method according to claim 1 wherein the step of engaging the clip comprises bringing a frictional section of the second inside surface of the second jaw into contact with the hinge region to prevent the clip from becoming disengaged from the first and second jaws during the compressing step.

6. The method according to claim 5 wherein the step of engaging the clip comprises bringing a first smooth section of the first inside surface of the first jaw into contact with the first leg of the clip to prevent the clip from being damaged during the compressing step, whereby the first leg is slidable along the first smooth section during the compressing step.

7. The method according to claim 6 wherein the step of engaging the clip comprises bringing a second smooth section of a second inside surface of the first jaw into contact with the interlocked clip region to prevent the clip from being damaged during the compressing step, whereby the interlocked clip region is slidable along the second smooth section during the compressing step.

8. The method according to claim 1 wherein the step of engaging the clip comprises bringing a smooth section of the first inside surface of the first jaw into contact with the first leg of the clip to prevent the clip from being damaged during the compressing step, whereby the first leg is slidable along the smooth section during the compressing step.

9. The method according to claim 1 wherein the step of engaging the clip comprises bringing a smooth section of a second inside surface of the first jaw into contact with the interlocked clip region to prevent the clip from being damaged during the compressing step, whereby the interlocked clip region is slidable along the smooth section during the compressing step.

10. The method according to claim 1 comprising the steps of:
    (a) disengaging the first and second jaws from the clip;
    (b) rotating the first and second jaws; and
    (c) grasping the clip with the first and second jaws by bringing the first jaw into contact with a first side of the hinge region and the second jaw into contact with a second opposing side of the hinge region.

11. The method according to claim 10 wherein the step of rotating the first and second jaws comprises rotating an elongate member attached to the first and second jaws.

12. The method according to claim 10 wherein the step of grasping the clip comprises bringing a first frictional section of the first inside surface of the first jaw into contact with the first side of the hinge region and bringing a second frictional section of the second inside surface of the second jaw into contact with the second opposing side of the hinge region.

13. The method according to claim 10 wherein the step of grasping the clip comprises bringing a first distal frictional section of the first jaw into contact with the first side of the hinge section and bringing a second distal frictional section of the second jaw into contact with the second opposing side of the hinge section.

14. The method according to claim 1 comprising the step of conveying a fluid through a sleeve attached to the first and second jaws to an outlet aperture of the sleeve disposed near the first and second jaws.

15. A method for unlatching a clip initially provided in a latched state, the clip comprising first and second arcuate legs joined at a hinge section, the first leg terminating at a hook section and the second leg terminating at an end section retained by the hook section in the latched state, the method comprising the steps of:
    (a) providing first and second jaws pivotably connected to each other and movable between an open position and a closed position wherein, at the closed position, the first and second jaws define a jaw gap therebetween, and at least a portion of the jaw gap increases in distance along a direction from a distal end of the jaws toward a proximal end of the jaws;
    (b) engaging the clip with the first and second jaws by bringing the first jaw into contact with the first leg of the clip and the second jaw into contact with the hook and hinge sections of the clip, with the hinge section contacting a proximal frictional section of the second jaw; and
    (c) compressing the clip by moving the first and second jaws toward their closed position, whereby the first leg of the clip begins to straighten and the end section of the second leg is released from the hook section of the first leg.

16. The method according to claim 15 comprising the steps of:

(a) disengaging the first and second jaws from the clip;
(b) rotating the first and second jaws; and
(c) grasping the clip with the first and second jaws by bringing the first jaw into contact with a first side of the hinge section and the second jaw into contact with a second opposing side of the hinge section.

17. The method according to claim 16 wherein the step of rotating the first and second jaws comprises rotating an elongate member attached to the first and second jaws.

* * * * *